United States Patent [19]

Mulla et al.

[11] 3,996,349

[45] Dec. 7, 1976

[54] ATTRACTANT COMPOSITIONS

[75] Inventors: Mir S. Mulla; Yih-Shen Hwang; Harold Axelrod, all of Riverside, Calif.

[73] Assignee: The Regents of the University of California, Berkeley, Calif.

[22] Filed: June 18, 1975

[21] Appl. No.: 588,085

[52] U.S. Cl. ................................................ 424/84
[51] Int. Cl.² ......................................... A01N 17/14
[58] Field of Search .................................... 424/84

[56] References Cited

UNITED STATES PATENTS 2,307,844  1/1943  McPhail .............................. 424/84

FOREIGN PATENTS OR APPLICATIONS 20,738  1964  Japan ................................. 424/84
23,439  1969  Japan ................................. 424/84

*Primary Examiner*—Sam Rosen
*Attorney, Agent, or Firm*—Donald W. Erickson

[57] ABSTRACT

Attractant compositions for synanthropic flies comprising tertiary amine, ammonia, linoleic acid, lower hydrocarbon carboxylic acid and indole or skatole.

7 Claims, No Drawings

ATTRACTANT COMPOSITIONS

This invention relates to attractant compositions. More particularly, this invention relates to attractant compositions for synanthropic flies which are prepared from readily available chemicals, economical and of uniform properties.

Synanthropic flies are insects having widespread distribution. They constitute a persistent nuisance to man, and domestic and wild animals. The level of nuisance varies in degree from simple annoyance to death due to infestation and blockage of vital air passages. These flies also play a significant role as vectors of disease agents to man and animals. Synanthropic flies belong to the order Diptera and include flies of such families as Chloropidae, Calliphoridae, Sarcophagidae, Anthomyiidae, Muscidae, and Drosophilidae. Examples of species include the *Hippelates* eye gnats, screw worm flies, flesh flies, the house fly, and fruit flies.

Because of the very widespread distribution, high fecundity and multiple generations of these flies each season, control programs relying exclusively on the use of insecticides have not been satisfactory. These control programs involve applying insecticides over entire infested areas and this practice is ecologically and economically costly. Moreover, broad coverage of insecticides results in the rapid development of acquired resistence to these agents. The use of an effective and economical attractant composition to reduce the area for insecticide treatment would be of considerable advantage and benefit, and will yield selective and ecologically sound control strategies.

It has been discovered that an effective and economical composition for attracting synanthropic flies is provided by a combination of a tertiary amine, ammonia, linoleic acid or oleic acid and indole or skatole adjusted to pH 5 to 8 by the addition of a lower hydrocarbon carboxylic acid. The attractant composition of the present invention can be used for control in conjunction with electrical insect traps or in combination with insecticides such as dimethyl 2,2-dichlorovinyl phosphate and others, and applied as spot or broadcast treatments.

In the preparation of the attractant compositions of the present invention, the compositions are prepared as an aqueous mixture which can be used as a liquid to attract the flies or in combination with a solid carrier such as cotton or other cellulosic material (such as powder cellulose and Alphacel), sugar, silicates, clays, corn cob grits, and the like. The aqueous mixture contains from 0.1 to 10% tertiary amine, 0.1 to 7% ammonia (as ammonium hydroxide), 0.005 to 1% of linoleic acid or oleic acid, 0.001 to 0.1% indole or skatole, by weight of the total mixture, and sufficient lower hydrocarbon carboxylic acids or inorganic acids to adjust the mixture to pH 5 to pH 8. Preferred percentages of the components are 0.1 to 5.0% amines, 0.5 to 5.0% ammonia, 0.01 to 1.0% linoleic (or oleic acid) acid, 0.001 to 0.1% indole or skatole and sufficient carboxylic acid to adjust the mixture to pH 6. For preparing solid formulations, the aqueous solution containing the various chemicals is soaked onto and/or blended with the solid carrier. The water may be removed by either air drying or freeze drying. Freeze drying has yielded very active formulations.

Suitable amines include the tertiary lower alkyl amines wherein the alkyl group contains 1 to 3 carbon atoms such as trimethylamine, triethylamine and dimethylethylamine. The term "lower hydrocarbon carboxylic acid", as used herein, refers to a hydrocarbon carboxylic acid of 2 to 7 carbon atoms, preferably acetic acid, propionic acid or n-butyric acid.

An attractant composition (A') of the present invention of an aqueous mixture of 1.2% trimethylamine, 0.8% ammonia, 0.3% linoleic acid, and 0.01% indole, acidified to pH 6.0 with acetic acid was tested for attractancy of *Hippelates collusor*, eye gnats, using the Citrus Research Center olfactometer, Mulla et al, Ann. Entomol. Soc. Amer. 53 834, (1960). The olfactometer consisted of four main parts: (1) eye gnat traps consisting of funnels and collection vials, (2) bait dishes, (3) a circular table with 20 holes and 8 mesh screen supporting the traps, and (4) an electric motor unit, speed controller, and reducer. The bait dishes were placed on the screens, test materials placed in the bait dishes, and the eye gnat traps inverted over them. The motor unit rotated the table at a speed of 0.25 rpm. The eye gnats which were attracted by the test materials flew under the table and crawled through the support screen into the trap collection vials where they were killed by a deposit of a knockdown insecticide (dimethyl 2,2-dichlorovinyl phosphate).

A standard batch of 1% fermented aqueous suspension of whole-egg powder (pH 6.0) showing potent attractancy was used along with the test materials for comparison. The standard fermented aqueous suspensions due to malodors are not suitable for use in control programs. The tests were run until at least an average of 50 eye gnats were captured by the standard material. This procedure usually required 1–2 hr. Empty traps and traps containing water did not catch any insects, showing that there was no random capture. The attractancies were expressed as mean percent of the number in the standard. The statistical significance of the differences among the test samples was calculated at 5% level by performing analysis of variance using Duncan's Multiple Range Test. The attractant composition (A') gave a mean attractancy of 111.3%. The foregoing composition without indole gave a mean attractancy of 46.6%. The foregoing composition containing 0.01% skatole in place of indole gave a mean attractancy of 79.4%. The results are based on 12 tests with 4 replicates in each test.

A second embodiment of the attractant composition containing 1.1% trimethylamine, 0.8% ammonia, 0.01% indole and 0.01% linoleic acid as an aqueous mixture adjusted to pH 6.0 using acetic acid was tested on house flies in conjunction with an electrocutor grid trap known as the Zap trap (Model AG-60). Each set of traps was placed about 5 feet apart. The attractant (100 ml.) was soaked onto cotton in a paper cup and covered with cheese cloth to exclude flies. All traps had the black light tubes removed, using the grid apparatus to kill the flies. The results of two sets of traps for a two day period are tabulated below.

| Day | Trap | Attractant Added | No. house flies | | | % of total | Other Diptera[r] |
| --- | --- | --- | --- | --- | --- | --- | --- |
| | | | Male | Female | Total | | |
| 1 | A | yes | 1,848 | 4,356 | 6,204 | 91.6 | 264 |
| | B | no | 210 | 360 | 570 | 8.4 | 30 |
| 2 | A | no | 648 | 432 | 1,080 | 47.1 | 0 |
| | B | yes | 243 | 972 | 1,215 | 52.9 | 27 |
| 1 | C | yes | 2,160 | 3,000 | 5,160 | 54.4 | 240 |
| | D | no | 1,584 | 2,736 | 4,320 | 45.6 | 144 |
| 2 | C | no | 1,320 | 3,120 | 4,440 | 40.2 | 30 |
| | D | yes | 1,500 | 5,100 | 6,600 | 59.8 | 50 |

[r]Other Diptera comprised small numbers of Fannia, Sarcophagidae and Calliphoridae; the majority, however, were small shiny-black Anthomyiidae.

Additional embodiments of the present invention are the following attractant compositions.

| Composition | Concentration (%) | | | | |
| --- | --- | --- | --- | --- | --- |
| | $Me_3N$ | $NH_3$ | Indole | Linoleic acid | AcOH |
| 8X | 9.2 | 6.6 | 0.08 | 0.3 | to pH 6.0 |
| 4X | 4.6 | 3.3 | 0.04 | 0.3 | to pH 6.0 |
| 2X | 2.3 | 1.6 | 0.02 | 0.3 | to pH 6.0 |
| 1X | 1.2 | 0.8 | 0.01 | 0.3 | to pH 6.0 |

The above four attractant compositions in aqueous phase were impregnated onto various substrates at the following proportions.

| Substrate and Amount (g) | | Attractant mixture (g) |
| --- | --- | --- |
| Promosoy 100 | 5 | 5 |
| Dried blood | 6 | 4 |
| Alphacel | 5 | 5 |
| Chicken whole-egg powder | 8 | 2 |

Quantities of each solid formulation was mixed with an equal amount of dimethyl 2-dichlorovinyl phosphate-sugar bait and tested against *H. collusor*. The UC Fly Bait (U.S. Pat. No. 3,846,557) was used as standard. The following table shows the attractancy of these preparations.

| Attractant Formulation | Mean attractancy (%) to eye gnats[1] | | | |
| --- | --- | --- | --- | --- |
| | 8X | 4X | 2X | 1X |
| Promosoy 100 | 20 | 20 | 16 | 18 |
| Dried Blood | 16 | 6 | 21 | 8 |
| Alphacel | 15 | 22 | 21 | 6 |
| Egg powder | 32 | 34 | 12 | 12 |

[1]Based on 4 replicates

The synthetic attractant compositions of the present invention absorbed onto inert organic and inorganic carriers, evaluated as such or evaluated after freeze drying to remove excess water, have been found to be highly attractive against eye gnats. Its attractancy, although not reaching the standard (UC Fly Bait) obtained by putrefaction and freeze-drying, is still considered high, because the standard batch used here is one of the most potent batches ever produced.

The attractant compositions of the present invention prepared from readily available synthetic chemicals have several advantages over attractant compositions prepared by putrefaction of complex proteins. With the synthetic attractant compositions herein, one can obtain standard products. This has not been possible with the putrefied product, where attractancy can vary 10–100 fold from one batch to the other, prepared under similar conditions. Also, the putrefied product has bad odors, discouraging its use in human residential areas and many other places.

Another embodiment of the present invention can be further illustrated by the following example. The 4X aqueous attractant mixture (430 g.) was mixed with Alphacel (130 g.), and the preparation was freeze-dried (using the procedure of U.S. Pat. No. 3,846,557 which is incorporated herein). The freeze-dried material was mixed with equal amount of dimethyl 2,2-dichlorovinyl phosphate-sugar bait and tested against *M. domestica*. The UC Fly Bait described above and mixed with equal amount of dimethyl 2,2-dichlorovinyl phosphate-sugar bait was used as standard. The following table shows the attractancy of the attractant preparation.

| Material | Mean no. of flies caught[1] |
| --- | --- |
| 4X attractant mixture on Alphacel | 297 |
| UC Fly Bait | 123 |

[1]Based on 4 replicates.

Freeze-drying yields a formulation with greater potency than non-dried or air-dried formulations. The toxicant-sugar bait above contained 0.01% dimethyl 2,2-dichlorovinyl phosphate.

In a further embodiment of the invention, the adjustment of the pH of the attractant composition is accomplished using an inorganic acid such as hydrochloric acid in lieu of a lower hydrocarbon carboxylic acid. The use of carboxylic acid is preferred, however, in that in addition to adjusting the pH, the carboxylic acid acts as a co-attractant in the compositions of the present invention.

The attractant compositions of the present invention can be used in conjunction or in mixture with insecticides such as dimethyl, $\beta,\beta,\beta$-trichloro-$\alpha$-hydroxyethyl phosphonate, 2-isopropoxyphenyl N-methylcarbamate, dimethyl 2,2-dichlorovinyl phosphate, dimethyl 3-hydroxyglutaconate dimethyl phosphate, 0,0-dimethyl-0-(2,4,5-trichlorophenyl)phosphorothioate, and the like to provide knockdown. The attractant compositions can be used in conjunction with traps such as electric grid traps or traps provided with a sticky, adhesive surface also.

What is claimed is:

1. An attractant composition for synanthropic flies which comprises an aqueous mixture of 0.1 to 10% tertiary lower alkylamine, 0.1 to 7.0% ammonia, 0.005 to 1% linoleic or oleic acid, 0.001 to 0.1% indole or skatole, and sufficient lower hydrocarbon carboxylic acids to adjust the aqueous mixture to pH 5 to pH 8, said percentages by weight of the total aqueous mixture.

2. An attractant composition according to claim 1 containing 0.1 to 5% of the amine, 0.5 to 5% ammonia, 0.01 to 1.0% linoleic acid, 0.001 to 0.1% indole or skatole and sufficient amount of lower carboxylic acids to adjust the mixture to pH 6.

3. An attractant composition according to claim 2, containing about 1% amine, 1% ammonia, 0.01% linoleic acid, 0.01% indole or skatole and sufficient amount of lower carboxylic acid to adjust the pH of the mixture to 6.

4. An attractant composition according to claim 1 wherein the amine is trimethylamine and the carboxylic acid is acetic acid, propionic acid or n-butyric acid.

5. An attractant composition according to claim 2 containing trimethylamine, ammonia, linoleic or oleic acid, indole and acetic acid.

6. An attractant composition according to claim 2 absorbed onto a solid carrier.

7. An attractant composition according to claim 6 subjected to freeze-drying.

* * * * *